United States Patent
Searcey et al.

(10) Patent No.: US 7,626,026 B2
(45) Date of Patent: Dec. 1, 2009

(54) PYRROLO-INDOLE AND PYRROLO-QUINOLINE DERIVATIVES AS PRODRUGS FOR TUMOUR TREATMENT

(75) Inventors: Mark Searcey, London (GB); Laurence Hylton Patterson, London (GB)

(73) Assignee: University of Bradford, Bradford (GB)

( * ) Notice: Subject to any disclaimer, the term of this patent is extended or adjusted under 35 U.S.C. 154(b) by 109 days.

(21) Appl. No.: 10/468,741

(22) PCT Filed: Feb. 22, 2002

(86) PCT No.: PCT/GB02/00796

§ 371 (c)(1), (2), (4) Date: Apr. 6, 2004

(87) PCT Pub. No.: WO02/068412

PCT Pub. Date: Sep. 6, 2002

(65) Prior Publication Data
US 2004/0157873 A1 Aug. 12, 2004

(30) Foreign Application Priority Data
Feb. 22, 2001 (EP) .................................. 01301636

(51) Int. Cl.
C07D 487/06 (2006.01)
C07D 487/02 (2006.01)
A61K 31/407 (2006.01)

(52) U.S. Cl. .................. 546/81; 548/433; 548/429; 514/411; 514/292

(58) Field of Classification Search .................. 546/81; 548/433, 429; 514/411, 292
See application file for complete search history.

(56) References Cited

U.S. PATENT DOCUMENTS

| | | | |
|---|---|---|---|
| 4,413,132 A | 11/1983 | Wierenga | |
| 5,448,869 A | 9/1995 | Unruh et al. | |
| 5,501,054 A | 3/1996 | Soltis et al. | |
| 5,679,432 A | 10/1997 | Holmquest et al. | |
| 5,688,426 A | 11/1997 | Kirkwood et al. | |
| 5,794,402 A | 8/1998 | Dumlao et al. | |
| 5,843,937 A | 12/1998 | Wang et al. | |
| 5,852,909 A | 12/1998 | Soltis et al. | |

FOREIGN PATENT DOCUMENTS

| | | |
|---|---|---|
| EP | 0 244 120 A2 | 11/1987 |
| EP | 0 563 475 A1 | 10/1993 |
| FR | 2 700 805 | 7/1994 |
| WO | 91/10024 | 7/1991 |
| WO | 97/01686 | 1/1997 |
| WO | WO-97/12246 | 4/1997 |
| WO | WO-97/32850 | 9/1997 |
| WO | WO-97/45411 | 12/1997 |
| WO | WO-98/52925 | 11/1998 |
| WO | WO-99/40056 | 8/1999 |

OTHER PUBLICATIONS

Moana Tersel et al Synthesis and Cytotoxicity of Amino-seco-DSA : An amino analogue fo DNA alkylating Agent Duocarmycin SA , 1999, vol. 64 pp. 5946-5943.*
Dale Boger et al "Reversed and sandwiched Analogs of Duocarmycin SA:" 1997, vol. 119 pp. 4987-4998.*
Dale boger et al Studies on the total Synthesis of CC-1065: Preparation of a Synthetic, Simlified 3-Carbamoyl- . . . 1987, vol. 52, pp. 1521-1530.*
Dorwald F. A. Side Reactions in Organic Synthesis, 2005, Wiley: VCH, Weinheim pg. IX of Preface and pp. 8 and 9.*
Abstract of Canadian Patent Application No. 2315569 A1, Feb. 2001.
Abstract of CH-009374, Jul. 22, 1976.
Abstract of GB-005435, Mar. 9, 1987.
Boger et al; J. Am. Chem. Soc. vol. 119, No. 21, 1997.
Boger et al; J. Org. Chem. 2000, 65, 4101-4111.
Boger et al; Chemical Reviews, 1997, vol. 97, No. 3.
Amishiro et al; Bioorganic & Medicinal Chemistry 8 (2000), 1195-1201.
J. Med. Chem., 1999, 42(4), 669-676.
Boger et al; Bioorganic & Medicinal Chemistry Letters 11 (2001) 221-2024.
Nagamura et al., Bioorganic & Medicinal Chemistry, vol. 4, pp. 1379-1391 (1996).
Forbes et al., J. Med. Chem., vol. 38, pp. 2524-2530 (1995).

(Continued)

*Primary Examiner*—Rita J Desai
(74) *Attorney, Agent, or Firm*—Dickstein Shapiro LLP

(57) ABSTRACT

Compounds of the general formula (I) or (IA) in which X is H, Y is a leaving group, $R^1$ and optionally also $R^3$ preferably being an aromatic DNA binding subunit are prodrug analogues of duocarmycin. The compounds are expected to be hydroxylated at the carbon atom to which X is joined, by cytochrome P450, in particular by CYP1B1, expressed at high levels in tumors. The prodrug is expected to be activated preferentially in tumor cells, where it will act as a DNA alkylating agent preventing cell division.

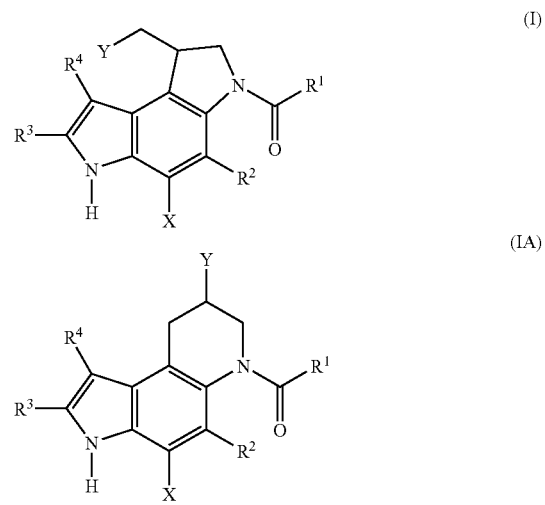

12 Claims, No Drawings

OTHER PUBLICATIONS

Borger et al., J. Org. Chem., vol. 62, pp. 8875-8891 (1997).
Macor et al., Tetrahedron Letters, vol. 38, pp. 1673-1676 (1997).
Muratake et al., Chem. Pharm. Bull., vol. 44, pp. 67-79 (1996).
Muratake et al., vol. 46, pp. 400-412 (1998).
Warpehoski et al., Tetrahedron Letters, vol. 27, pp. 2735-2738 (1986).
Rawal et al., J. Org. Chem., vol. 52, pp. 19-28 (1987).
Boger et al., Chem. Rev., vol. 97, pp. 787-828 (1997).
Boger et al., Synthesis, No. SI, pp. 1505-1509 (1999).
Boger et al., J. Am. Chem. Soc., vol. 113, No. 10, pp. 3980-3983 (1991).
Murray et al., Cancer Research, vol. 57, pp. 3026-3031 (1997).
Patterson et al., Anti-Cancer Drug Design, vol. 14, pp. 473-486 (1999).

* cited by examiner

PYRROLO-INDOLE AND PYRROLO-QUINOLINE DERIVATIVES AS PRODRUGS FOR TUMOUR TREATMENT

The present invention concerns aromatic oxidation/hydroxylation activated prodrugs, particularly anti-tumour prodrugs and those which are specifically activated by the oxidation/hydroxylation activities of the cytochrome P450 family of enzymes.

Many conventional cytotoxic drugs are known that can be used for therapeutic purposes. However, they typically suffer from the problem that they are generally cytotoxic and therefore may affect cells other than those that are required to be destroyed. This can be alleviated to some extent by the use of targeted drug delivery systems, for example direct injection to a site of tumourous tissue or, e.g. binding the cytotoxic agent to an antibody that specifically recognises an antigen displayed only on the cancer cell surface. Alternatively, electromagnetic radiation may be used to cause chemical alteration in an agent at a desired site such that it becomes cytotoxic. However, all of these techniques have, to a greater or lesser extent, certain limitations and disadvantages.

The compound (+)—CC-1065 and the duocarmycins are naturally occurring representatives of a class of DNA alkylating agents. The naturally occurring compounds consist of a DNA alkylating unit based upon a pyrrolo[3,2-e]indole core, with one or two sub units, conferring DNA binding capabilities. CC-1065 and duocarmycin A comprise a spirocyclic cyclopropane group responsible for the DNA alkylation properties. Duocarmycin $B_2$, $C_2$ and $D_2$ are believed to be precursors for cyclopropane actives, and comprise a substituted (by a leaving group) methyl group at the eight position on the dihydro pyrrole ring. CC-1065 has been synthesised by various routes, summarised by Boger et al. in Chem. Rev. 1997, 97, 787-828.

In U.S. Pat. No. 4,413,132 the first synthesis of the left hand sub-unit of CC-1065 was described. The synthesis is based on a Winstein Ar-3' alkylation in which the cyclopropane ring is introduced. In a previous step, the A ring (of the indole core) is introduced by reaction of an aniline with an α-thiomethylester using chemistry based on Gassman's Oxindole synthesis. The aniline has a protected phenolic hydroxyl group ortho to the $NH_2$ group, which, in the final product, is believed to be crucial for DNA alkylation. CC-1065 has broad antitumour activity but is too toxic against normal cells to be clinically useful. Attempts have been made to target the delivery of CC-1065 and analogues by conjugating the drug via the DNA binding subunit to polymers, or specific binding agents such as antibodies or biotin described in U.S. Pat. No. 5,843,937. Boger et al in Synthesis 1999 SI, 1505-1509 described prodrugs of 1,2,9,9a-tetrahydrocyclopropa(c)benz[e]indol-4-one, in which the cyclopropane ring-opened version of the compounds were derivatised by reaction of the phenolic group to form esters and carbamates.

In J. Am. Chem. Soc. (1991), 113, 3980-'83 Boger et al describe a study to identify features of CC-1065 analogues contributing to the selectivity of the DNA-alkylation. The compounds tested in vitro had alkylating subunits based on 2,3-dihydroindole and included the 6-deshydroxy analogues. These were shown to have some DNA alkylating properties though at concentrations $10^4$ times higher than that of the 6-hydroxy compounds.

Tercel et al, in J. Org. Chem. (1999) 64, 5946-5953 describe amino analogues of CC-1065 (i.e. in which the phenolichydroxy of the B-ring is replaced by amino). These are synthesised by nitrating the benzene ring in a late stage intermediaet having a methylol group attached to the dihydropyrrole ring.

The present invention relates to precursors of CC-1065 and its analogues, which do not have the hydroxyl group in the B ring of the alkylating sub unit, and which are hence inactive as DNA alkylating agents themselves, as well as their synthesis and intermediates used therein.

It has been reported (Murray, G. I. et al., 15 Jul. 1997, Cancer Research, 57m 3026-3031 and WO-A-9712246) that the enzyme CYP1B1, a member of the cytochrome P450 (CYP) family of xenobiotic metabolising enzymes, is expressed at a high frequency in a range of human cancers, including cancers of the breast, colon, lung, oesophagus, skin, lymph node, brain and testes, and that it is not detectable in normal tissues. This led to the conclusion that the expression of cytochrome P450 isoforms in tumour cells provides a molecular target for the development of new antitumour drugs that could be selectively activated by the CYP enzymes in tumour cells, although no drug examples were given. A number of other CYP isoforms have been shown to be expressed in various tumours. Many of the CYP's expressed in tumours are mentioned in Patterson, L H et al, (1999) Anticancer Drug Des. 14(6), 473-486.

In WO-A-99/40056 prodrugs of styrene- and chalcone-derivatives are described. The respective hydroxylated forms of the prodrugs, formed in situ, are potent tyrosine kinase (TK) inhibitors. Inhibition of TK activity contributes to tumour inhibition and cell destruction. The prodrugs were shown to be activated by microsomal preparations expressing CYP1B1 enzyme, and to have cytotoxic activity against cell lines expressing the same enzyme, whilst having much lower cytotoxic activity against cell lines not expressing the enzyme.

The present invention is directed to a new class of prodrugs which are expected to be hydroxylated in situ by CYP enzymes, in particular enzymes expressed at high levels in tumours as described in Patterson L H, et al, op. cit. In particular the prodrugs are believed to be metabolisable by CYP1B1enzyme. Some of the compounds are new. The present invention relates to the first therapeutic use of a broad range of compounds.

There is provided according to the first aspect of the invention the new use of a compound of the general formula I or a salt thereof in the manufacture of a composition for use in a method of treatment by therapy of an animal:

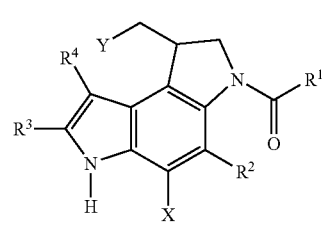

I

-continued

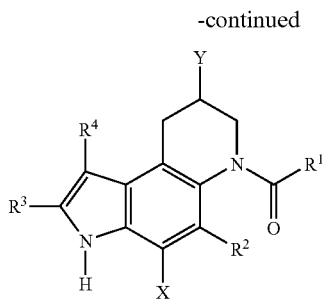

IA in which X is H;
Y is a leaving group
$R^1$ is —Ar, —$NH_2$, $R^8$ or $OR^8$;
$R^2$ and $R^4$ are each independently selected from H, $C_{1-4}$ alkyl, —OH, $C_{1-4}$ alkoxy, —CN, Cl, Br, I, —$NO_2$, —$NH_2$, —$NHCOR^9$, —$NHCOOR^9$, —COOH, —$CONHR^9$ and —$COOR^9$;
$R^3$ is selected from H, $C_{1-4}$ alkyl, —OH, $C_{1-4}$ alkoxy, —CN, Cl, Br, I, —$NO_2$, —$NH_2$, —$NHCOR^9$, —$NHCOOR^9$, —COOH, —$CONHR^9$, —$COOR^9$ and $COAr^{10}$;
$R^8$ and, $R^9$ are independently selected from $C_{1-4}$ alkyl, optionally substituted phenyl, $C_{7-12}$-aralkyl, optionally substituted heteroaryl and ligands;
Ar is selected from

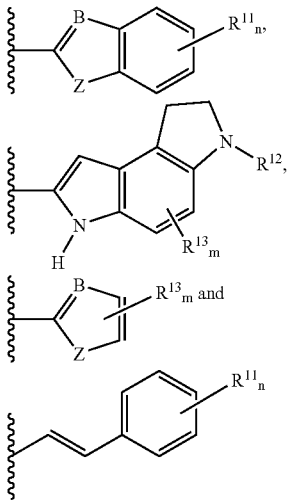

in which B is N or $CR^{14}$;
Z is O, S —CH═CH— or NH;
the or each $R^{11}$ is selected from OH, $C_{1-4}$ alkoxy, $C_{1-4}$ alkyl, —$NO_2$, —$NH_2$, —$NHR^{10}$, —$NR^{10}_2$, —$N^+R^{10}_3$, —CN, Cl, Br, I, —$NHCOR^{15}$, —COOH, —$CONHR^{16}$, —$NHCOOR^{16}$ and $COOR^{16}$;
n is an integer in the range 0 to 4;
the or each $R^{10}$ is selected from $C_{1-4}$ alkyl, optionally substituted phenyl, $C_{7-12}$-aralkyl, optionally substituted heteroaryl and ligands;
$R^{12}$ is H, —$COAr^1$, —$CONH_2$, —COOH, —$COR^{16}$ or —$COOR^{16}$;
the or each $R^{13}$ is selected from OH, $C_{1-4}$ alkoxy, $C_{1-4}$ alkyl, —$NO_2$, —$NH_2$, —$NHR^{10}$, —$NR^{10}_2$, —$N^+R^{10}_3$, —CN, Cl, Br, I, —$NHCOR^{15}$, —COOH, —$CONHR^{16}$, —$NHCOOR^{16}$ and —$COOR^{16}$;

m is 0, 1 or 2;
$R^{14}$ is selected from OH, $C_{1-4}$ alkoxy, $C_{1-4}$ alkyl, —$NO_2$, —$NH_2$, —CN, Cl, Br, I, —$NHCOR^{15}$, —COOH, —$CONHR^{16}$, —$NHCOOR^{16}$—$COOR^{16}$ and H;
$R^{15}$ is selected from $C_{1-4}$ alkyl, optionally substituted phenyl, optionally substituted heteroaryl, $C_{7-12}$ aralkyl, $Ar^1$ and ligands;
$R^{16}$ is selected from $C_{1-4}$alkyl, optionally substituted phenyl, $C_{7-12}$-aralkyl, optionally substituted heteroaryl and ligands;
$Ar^{10}$ is

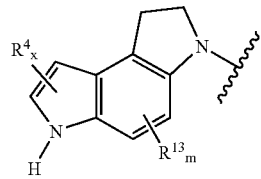

in which x is 0, 1 or 2;
$Ar^1$ is selected from the same groups as Ar; provided that no more than one group $R^{11}$ or $R^{13}$ in any one ring includes a group $Ar^1$.

The animal which is treated is generally a human, although the compounds may also have veternary use. The indication treated is generally cancer, including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The tumour may, for instance, be defined s as a tumour expressing high levels of CYP1B1.

In the invention a group $Ar^1$ is preferably

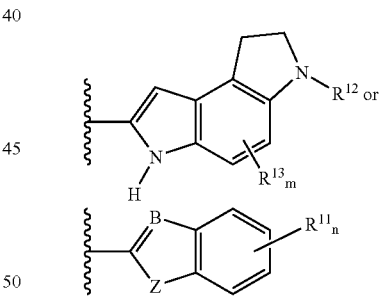

In the invention, the leaving group Y is, for instance, a group which has utility as a leaving group in nucleophilic substitution reactions. Suitable examples of such groups are —$OCOOR^5$, —$OCONHR^6$, Cl, Br, I, or —$OSOOR^7$, in which $R^5$, $R^6$ and $R^7$ are independently selected from $C_{1-4}$alkyl, optionally substituted phenyl, $C_{7-12}$-aralkyl and optionally substituted heteroaryl. Most preferably the leaving group is a halogen atom, preferably chlorine.

Optional substituents in phenyl, aralkyl and heteroaryl groups are, for instance, $C_{1-4}$-alkyl, halogen, hydroxyl, $C_{1-4}$-alkoxy, —$NH_2$, —$NHR^{10}$—, —$NR^{10}_2$, —$N^+R^{10}_3$, —$NO_2$—, —CN, —COOH, —$NHCOR^{15}$, —$COOR^{16}$, —$NHCOOR^{16}$$CONHR^{16}$ etc.

In the present invention the term ligand includes a group having specific targeting characteristics, useful for instance in antibody or gene-directed enzyme prodrug-type environments. A ligand may be an oligopeptide, biotin, avidin or streptavidin, a polymeric group, an oligonucleotide or a protein. Preferably it has specific binding characteristics such as an antibody or fragment, an antigen, a sense or anti-sense oligo-nucleotide, or one of avidin, streptavidin and biotin, that is it is one component of a specific binding pair. Alternatively it may be a group designed for passive targeting, such as a polymeric group, or a group designed to prolong the stability or reduce immunogenicity such as a hydrophilic group. U.S. Pat. No. 5,843,937 discloses suitable ligands for conjugating to these types of actives and methods for carrying out the conjugation.

In a pharmaceutically active compound $R^1$ is other than $OR^8$. In general, for optimised DNA binding ability, the group $R^1$ in a compound of the general formula I and IA is a group Ar and/or the group $R^3$ is a group $Ar^{10}$. Often the group $R^1$ may include two aromatic groups joined to one another. In such compounds, one of the groups $R^{11}$ of the Ar group, or the group $R^{12}$, as the case may be, is a group $Ar^1$. Whilst for some compounds it may be desirable for three or more such aromatic groups to be linked, it is preferred that there is one group Ar and either one group $Ar^{10}$, or, more preferably, one group $Ar^1$. Thus in a group $Ar^1$ which is a pyrrolo-dihydroindole type of group, the group $R^{12}$ should be other than a group —$COAr^1$. In a group $Ar^1$ which is one of the other types of group there should either be no substituents $R^{11}$, or $R^{13}$ as the case may be, or, if there are any substituents, such substituents should not include a group $Ar^1$.

According to one embodiment of the invention, the substituent Ar is a group

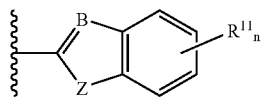

In such groups Ar, B is preferably $CR^{14}$. $R^{14}$ is preferably H. The definition of Z is preferably NH, although furan (Z is O) and thiophene (Z is 5) analogues had been generated for conjugation to DNA alkylating units and may have useful DNA binding characteristics. Similarly, in a group $Ar^1$, the groups B and Z are selected amongst the same preferable groups. Preferably n is at least 1 and one of the groups $R^{11}$ is —$NHCOAr^1$. In this embodiment $Ar^1$ is preferably a group

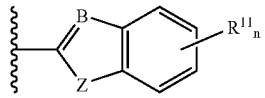

in which B and Z are the same as in Ar.

In another embodiment the substituent Ar is a group

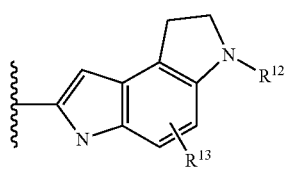

Preferably $R^{12}$ in such a group Ar is a group —$COAr^1$ in which $Ar^1$ preferably is the same type of group. Alternatively $R^{12}$ in such a group is other than —$COAr^1$ and $R^3$ is —$COAr^{10}$.

In both groups Ar and $Ar^1$, m in the indole type group is preferably zero.

In Ar and $Ar^1$, there may be several substituents $R^{11}$. Most preferably such substituents are selected amongst $C_{1-4}$-alkoxy groups.

In compounds of the formula I, the core indole ring of the DNA alkylating sub-unit is preferably unsubstituted in the benzene ring ($R^2$ is hydrogen), whilst the pyrrole ring may be unsubstituted ($R^3$ and $R^4$ are both hydrogen, or one or both of them represents a group —$COOR^{10}$, or a $C_{1-4}$-alkyl, preferably methyl).

In the compounds of the formula I, X is H. It is believed that, hydroxylation of the compound will occur in situ at the carbon atom to which X is attached, thereby activating the compound enabling it to act as a DNA alkylating agent.

Many of the compounds of the general formula I and IA, as well as amine protected precursors thereof are believed to be novel compounds. According to a further aspect of the invention there is provided a new compound of the general formula II or IIA or a salt thereof

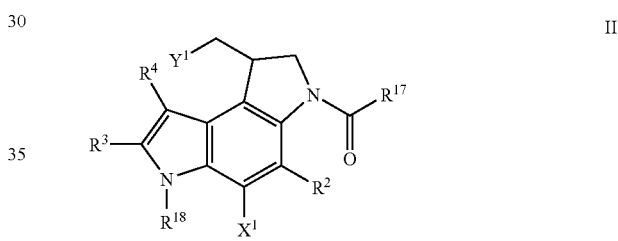

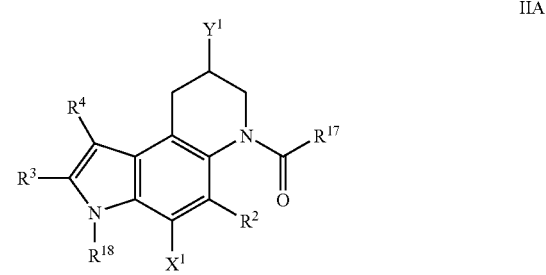

in which $R^2$, $R^3$ and $R^4$ are as defined for formula I and IA above;

$X^1$ is H;

$Y^1$ is a leaving group;

$R^{18}$ is H or an amine protecting group;

$R^{17}$ is $R^8$, —$OR^8$—$NH_2$ or $Ar^2$;

$R^8$ is as defined above for formula I and IA;

$Ar^2$ is selected from

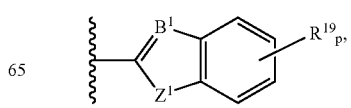

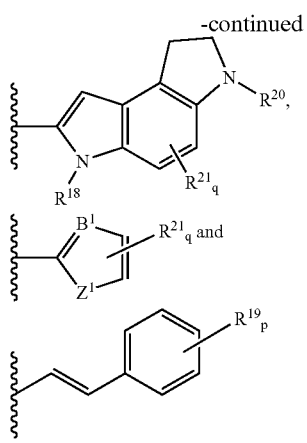

in which $B^1$ is N or $CR^{40}$;

$R^{40}$ is selected from H, OH, $C_{1-4}$-alkoxy, $C_{1-4}$-alkyl, $-NO_2$, $-NH_2$, $-CN$, Cl, Br, I, $-NHCOR^{22}$, $-COOH$, $-CONHR^{23}$, $-NHCOOR^{23}$ and $-COOR^{23}$.

$Z^1$ is O, S, $-CH=CH-$ or $NR^{18}$;

the or each $R^{19}$ is selected from, OH, $C_{1-4}$ alkoxy $C_{1-4}$ alkyl, $NO_2$, $-NHR^{18}$, $-NHR^{23}$, $-NR^{23}_2$, $-N^+R^{23}_3$, $-CN$, Cl, Br, I, $-NHCOR^{22}$, $-COOH$, $-CONHR^{23}$ and $-COOR^{23}$;

p is an integer in the range 0 to 4;

$R^{20}$ is H, $-COAr^3$, $-CONH_2$, $-COOH$, $-COR^{23}$ or $-COOR^{23}$;

the or each $R^{21}$ is selected from OH, $C_{1-4}$ alkoxy $C_{1-4}$ alkyl, $NO_2$, $-NHR^{18}$, $-NHR^{23}$, $-NR^{23}_2$, $-N^+R^{23}_3$, $-CN$, Cl, Br, I, $-NHCOR^{22}$, $-COOH$, $-CONHR^{23}$ and $-COOR^{23}$;

q is 0, 1 or 2

$R^{22}$ is selected from $C_{1-4}$ alkyl, optionally substituted phenyl, optionally substituted heteroalkyl, $C_{7-12}$ aralkyl, ligands and $Ar^3$ $R^{23}$ is selected from $C_{1-4}$alkyl, optionally substituted phenyl, $C_{7-12}$-aralkyl and optionally substituted heteroaryl; and $Ar^3$ is selected from the same groups as $Ar^2$ provided that no more than one $R^{19}$ or $R^{21}$ in any one ring includes a group $Ar^3$.

$Ar^3$ is preferably.

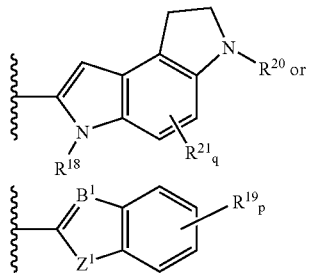

Compounds of the formula II or IIA, in which primary or secondary amine nitrogen atoms are protected are generally deprotected before being used in pharmaceutical compositions. Examples of amine protecting groups are benzyl, benzyloxycarbonyl, tertiary butyloxycarbonyl (BOC), fluorenyl-N-methoxy-carbonyl (FMOC) and 2-[biphenylyl-(4)]-propyl-2-oxycarbonyl. In particularly useful services of compounds of the general formula II and IIA $R^{17}$ is $-OR^8$ and $R^8$ is an amine protecting group different to $R^8OCO-$. In another preferred services $R^{17}$ is other than $DR^8$. Where more than one such amine group is protected in the molecule, the protecting groups may be the same or different.

The present invention further provides pharmaceutical compositions comprising compounds of the formula I or IA or salts and a pharmaceutically acceptable excipient. Pharmaceutical compositions may be suitable for intramuscular, intraperitoneal, intrapulmonary, oral or, most preferably, intravenous administration. The compositions contain suitable matrixes, for example for controlled or delayed release. The compositions may be in the form of solutions, solids, for instance powders, tablets or implants, and may comprise the compound of the formula I in solid or dissolved form. The compound may be incorporated in a particulate drug delivery system, for instance in a liquid formulation. Specific examples of suitable excipients include lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate. Solid compositions may take the form of powders and gels but are more conveniently of a formed type, for example as tablets, cachets or capsules (including spansules). Alternative, more specialised types of formulation including liposomes, nanosomes and nanoparticles.

Compounds of the formula I and IA may be synthesised using techniques analogous to those summarised by Boger et al 1997, op. cit. It is convenient to form the DNA alkylating sub unit in one series of steps and to attach this through the nitrogen atom of the dihydro-pyrrole or tetrahydroquinoline, as the case may be, (C) ring to the rest of the molecule. The DNA alkylating sub-unit may be conjugated to DNA binding sub-units synthesised as described in Boger et al, 1997 op. cit., for instance the PDE-I and PDE-II sub-units described in that reference. The DNA binding subunits are the groups including Ar, $Ar^1$ and $Ar^{10}$.

According to a further aspect of the invention there is provided a new synthetic method in which a compound of the formula IV or IVA

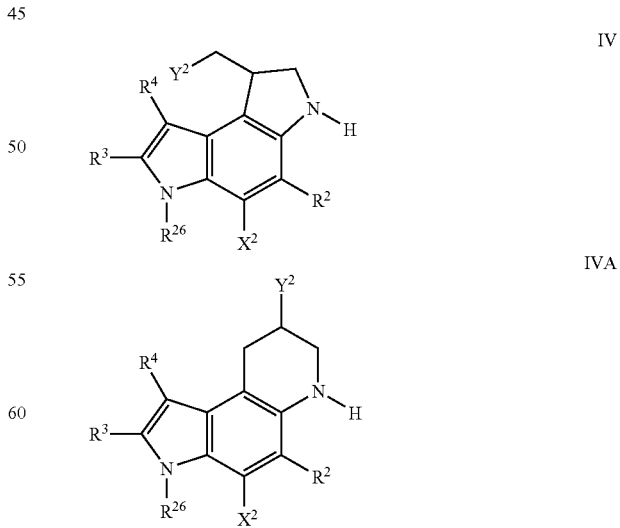

in which $X^2$, $R^2$ and $R^4$ are as defined above;

$R^{37}$ is selected from the same groups as $R^3$;

$Y^2$ is a leaving group or a hydroxyl or protected hydroxyl group; and $R^{26}$ is an amine protecting group;

is reacted with a compound of the general formula V $$R^{27}COY^3 \quad\quad V$$

in which $R^{27}$ is selected from $C_{1-4}$-alkyl, optionally substituted phenyl, $C_{7-12}$-aralkyl, optionally substituted heteroaryl and $Ar^4$;

$Ar^4$ is selected from

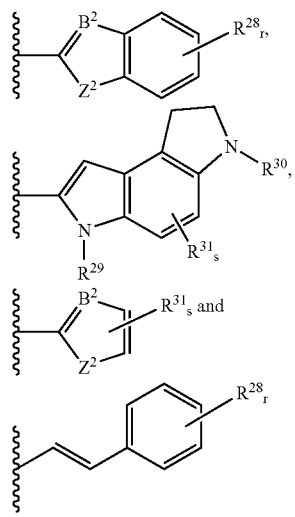

in which $B^2$ is N or $CR^{32}$;

$Z^2$ is O, S, —CH=CH— or $NR^{33}$;

the or each $R^{28}$ is selected from $C_{1-4}$-alkoxy, $C_{1-4}$-alkyl, $NO_2$, CN, Cl, Br, I, —$NHR^{33}$, —$NR^{36}{}_2$, —$N^+R^{35}{}_3$—, —NHCOR$^{34}$, —COOH, —CONHR$^{35}$ and —COOR$^{35}$;

r is an integer in the range 0 to 4;

$R^{29}$ is an amine protecting group;

$R^{30}$ is an amine protecting group, —$CONH_2$, —COOH, —$COR^{35}$ or —$COAr^5$;

the or each $R^{31}$ is selected from $C_{1-4}$-alkoxy, $C_{1-4}$-alkyl, $NO_2$, CN, Cl, Br, I, —$NHR^{33}$, —$NR^{36}{}_2$, —$N^+R^{36}{}_3$—, NHCOR$^{34}$, —COOH, —CONHR$^{35}$ and —COOR$^{35}$;

s is 0, 1 or 2;

$R^{32}$ is selected from H, $C_{1-4}$-alkoxy, $C_{1-4}$-alkyl, $NO_2$, CN, Cl, Br, I, NHCOR$^{34}$, —COOH, —CONHR$^{35}$, —NHCOOR$^{35}$ and COOR$^{35}$;

the or each $R^{33}$ is an amine protecting group;

$R^{34}$ is selected from $Ar^5$, $C_{1-4}$-alkyl, optionally substituted phenyl, $C_{7-12}$-aralkyl, optionally substituted heteroaryl and ligands;

$R^{35}$ is selected from $C_{1-4}$-alkyl, optionally substituted phenyl, $C_{7-12}$-aralkyl, optionally substituted heteroaryl and ligands;

each $R^{36}$ is selected from $C_{1-4}$-alkyl, optionally substituted phenyl, $C_{7-12}$-aralkyl, optionally substituted heteroaryl and H $Ar^5$ is selected from the same groups as $Ar^4$; and $Y^3$ is a leaving group, provided that no more than one $R^{28}$ or $R^{31}$ in any one ring includes a group $Ar^5$.

$Ar^5$ is preferably

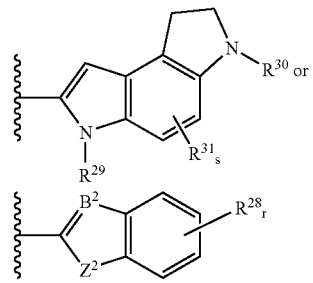

$Y^3$ is, for instance, selected amongst the preferred leaving groups listed above for Y. Most suitably the definition of $Y^3$ is Cl. Alternatively, the group $Y^3$ may be OH. In this case, it may be necessary to include a coupling agent to assist in the coupling reaction.

The reaction between the compound of the general formula IV or IVA and the carboxylic acid or derivative of the general formula V is carried out under conditions allowing such coupling to take place. Such conditions are similar to those generally used for formation of peptide bonds, for instance as used in peptide synthetic methods.

$Y^2$ is a hydroxy group or a leaving group, which may be the same as Y or may be converted to Y in a subsequent step.

Where, in the product, $R^3$ is a different group to $R^{37}$, the $R^{37}$ group is subsequently derivatised to generate the desired group $R^3$. This is often the case where, for instance, $R^3$ is a group $Ar^{10}$ or —$CONHR^9$. To produce compounds of that type the group $R^{37}$ is, for instance, —COOH or —COOR$^{10}$ and is reacted, optionally after hydrolysis/deprotection of a group —COOR$^{10}$, with an appropriate amine compound ($R^9NH_2$ or $Ar^{10}H$), optionally in the presence of coupling agents, to produce the amide linked compound.

After the coupling process, it may be desirable to deprotect one or more of the protected amine groups. If further reaction, for instance with other derivatising agents such as glycosyl compounds, peptides, polymers etc is desired through any such amine groups, it may be desirable to deprotect only those to which subsequent reaction to to take place, whilst retaining the other amine groups in a protected form. Selection of suitable amine protecting groups and protection and deprotection protocols may be made using techniques commonly utilised in peptide chemistry.

It is believed that some of the intermediates of the general formula IV or IVA may be novel compounds. According to a further aspect of the invention, there is provided a novel compound of the general formula III or IIIA

III

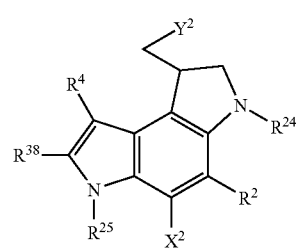

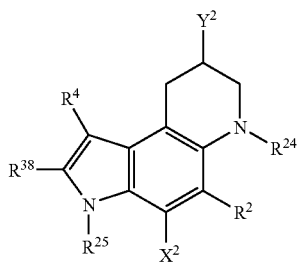

IIIA in which $R^2$ and $R^4$ are as defined for formula I and IA above;

$R^{38}$ is selected from the same groups as $R^3$;

$X^2$ is H;

$Y^2$ is a leaving group or a hydroxyl or protected hydroxyl group; and $R^{24}$ and $R^{25}$ are each H or an amine protecting group.

In compounds of the general formula III and IIIA, in the compound ready for reaction with a carboxylic acid derivative, for instance of the general formula V, $R^{24}$ is H, whilst $R^{25}$ should be an amine protecting group. Precursors for such compounds may have both ring nitrogen atoms in protected form, that is in which $R^{25}$ and $R^{24}$ represent protecting groups. In such compounds, since it is desired for the compound to be capable of derivatisation at just one of the nitrogen atoms, preferably $R^{24}$ and $R^{25}$ represent different protecting groups.

In compounds of the formula III and IIIA, the group $Y^2$ may be selected amongst those defined above for leaving group Y. The nature of the group $Y^2$ should be selected having regard to the nature of the reagent with which the compound of the formula IV or IVA, as the case may be, is to react in a subsequent step. Suitable examples of leaving group $Y^2$ are selected from those listed above for Y.

The compound of the formula III may be prepared in a preliminary step using as the starting material an aniline compound having a leaving group substituent $Y^4$ at the carbon atom ortho to the amine group substituent, and an N-substituent which is a trans 2-propen-1-yl group —CH$_2$CH=CHY$^5$, in which $Y^5$ is hydrogen or a group which is the same as $Y^2$ or may be converted to into $Y^2$ in a subsequent step in which the aniline derivative is reacted under cyclisation conditions, to form a dihydropyrrole ring. Preferably in the cyclisation reaction a halogen $Y^5(=Y^2)$ substituent is retained. The group $Y^4$ should be a radical leaving group, such as halogen, preferably I or Br. Suitable radicals for carrying out the cyclisation reaction where $Y^5$ is hydrogen are nitroxy compounds such as 2,2,6,6-tetramethylpiperidinyloxy (TEMPO). Where $Y^5$ is a radical leaving group (gY$^2$) the reaction may be carried out in the presence of a radical derived from azoisobutyronitrile (AIBN). In this step $Y^5$ does not leave. Suitable catalysts for a radical cyclisation step are tin hydride compounds such as tributyl tin hydride. This synthetic pathway is illustrated in Examples 1 and 3.

The compound of the general formula IIIA may be formed by cyclisation of an aniline compound having a radical leaving group $Y^4$ substituent ortho to the amine group and an N-substituent which is a 2-propen-1-yl group, preferably a trialkyl tin radical, under cyclisation conditions to form an intermediate dihydroquinonone. The cyclisation reaction is conducted in the presence of suitable catalysts which are, for instance, palladium complexes such as tetrakis (triphenylphosphine) palladium (0), bis(triphenyl phosphine) palladium (II) chloride or palladium (II) acetate. The dihydroquinonine intermediate is oxidised to form a further intermediate which is an epoxide, for instance using a peroxide reagent. The epoxide intermediate is reduced using a suitable selective reducing agent such as a dialkyl aluminium hydride to produce the corresponding alcohol which is subsequently halogenated, for instance using carbon tetrachloride/triphenyl phosphine. This reaction is illustrated in Examples 2 and 4.

The starting compound for such reactions may be represented by the general formula VI

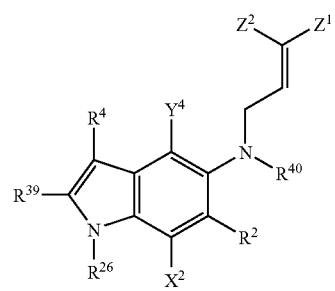

VI in which $R^2$, $R^4$, $R^{26}$, and $X^2$ are the same as in the compound of the formula IV;

$R^{39}$ is selected from the same groups as $R^3$;

$R^{40}$ is an amine protecting group different from $R^{26}$, one of $Z^1$ and $Z^2$ is $Y^5$ and the other is H;

$Y^5$ hydrogen, or is a leaving group which is the same as or different to $Y^2$; and $Y^4$ is a radical leaving group.

$Y^4$ is preferably selected from Cl, Br and I.

The compound of the general formula VI may be produced by alkylation of the sodium salt of the corresponding amiline derivative with a cis or trans-1,3-dihalo prop-2-ene compound. The cis starting material produces a compound of the general formula IV in which $Z^2$ is $Y^5$, the trans stating material a product VI in which $Z^1$ is $Y^5$. An allyl reagent produces a compound VI in which $Y^5$ is hydrogen.

The carboxylic acid derivative of the general formula V may be synthesised using the methods generally described in Boger et al, 1997 op.cit, for instance PDE-I and PDE-II may be synthesised using the Umezawa synthesis, the Rees-Moody synthesis, the Magnus synthesis, the Cava-Rawal synthesis, the Boger-Coleman synthesis, the Sundberg synthesis, the Martin synthesis, the Tojo synthesis. Indole-2-carboxylic acid is commercially available. Other analogues of the DNA binding sub-units of the duocarmycins, and reactive carboxylic acid derivatives thereof are described by Boger et al, op.cit. and in U.S. Pat. No. 5,843,937.

Two specific examples of compounds of the general formula I and II are

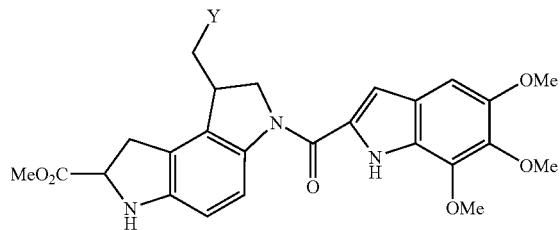

VII

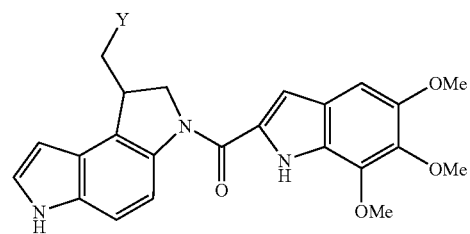

VIII

Two specific examples of a compound of the general formula IA and IIA are:

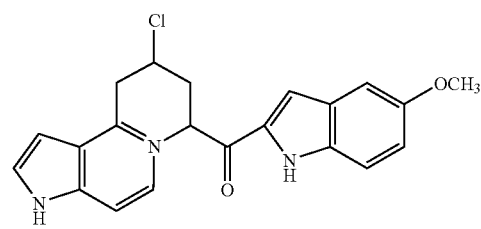

IX

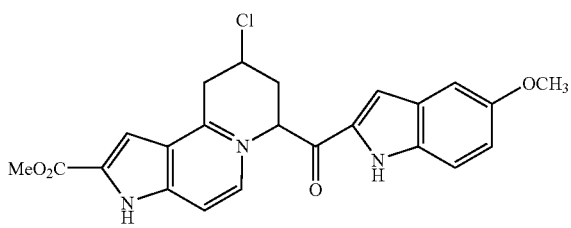

X

Other examples are ethyl rather than methyl esters of compounds VII and X.

The present invention relates to the creation of a range of prodrugs that have little or no cytotoxic effects when in their normal state, but are highly cytotoxic (i.e. have a substantially increased cytotoxicity) when activated by oxidation or hydroxylation by CYP enzymes. This provides for a self-targeting drug delivery system in which a non cytotoxic (or negligibly cytotoxic) compound can be administered to a patient, for example in a systemic manner, the compound then being activated at the site of the tumour cells (intratumoural activation) to form a highly cytotoxic compound which acts to kill the tumour cells. The fact that the CYP isoforms are not expressed by normal cells mean that the activation of the compound only occurs at the site of the tumour cells and therefore only tumour cells are affected, thus providing a self-targeting system.

The prodrugs of the present invention have the distinct advantage of being useful in the treatment of tumours at any site in the body, meaning that even tumours that have undergone metastasis (which are normally not susceptible to site specific therapies) may be treated.

The prodrug may be an antitumour prodrug. Examples of tumours include cancers (malignant neoplasms) as well as other neoplasms e.g. innocent tumours. The prodrug may be activated by hydroxylation by isoforms of cytochrome P450's.

In a variation of the normal procedure which relies upon CYP expression within tumour cells to effect selective hydroxylation and hence activation of the prodrugs, the selectivity between tumour tissue and normal tissue can be enhanced in a two part procedure. Thus (a) infecting tumor cells with a viral vector carrying a cytochrome P450 gene and a cytochrome P450 reductase gene, wherein expression of cytochrome P450 gene and cytochrome P450 reductase gene by tumor cells enables the enzymatic conversion of a chemotherapeutic agent to its cytotoxic form within the tumor, whereby the tumor cells become selectively sensitized to the prodrug chemotherapeutic agent (b) contacting tumor cells with the prodrug chemotherapeutic agent whereby tumor cells are selectively killed.

These prodrugs are pyrrolodihydroindole (general formula I) or pyrrolo tetrahydroquinoline (general formula IA) derivatives. Their specific use as antitumour prodrugs has not been previously suggested or disclosed, nor has the suggestion that they are prodrugs having an activated hydroxylated form. Where compounds of formula (I) have been previously identified and made, they have not been identified as anti-tumour agents due to their poor (or negligible) cytotoxicity. Thus the intratumoural hydroxylation of the prodrugs of the present invention provides them with a surprising and unexpected efficacy.

Hydroxylated forms of the prodrugs are potent DNA alkylating agents that bind in the minor groove of DNA and alkylate the purine bases at the N3 position. As such, they are potent cytotoxic agents whose exact biological mechanism of action is unknown but involves the disruption of template and other functions of DNA. General inhibition of template function of DNA will affect and be generally cytotoxic to all dividing cells in the body and lead to unacceptable side effects in a therapeutic setting. However, the targetted production of hydroxylated forms only in tumour cells that overexpress particular isoforms of cytochrome P450's will lead to a specific cytotoxic effect only in those cells. The non-hydroxylated forms are essentially non-toxic to all cells.

The following examples illustrate the invention:

EXAMPLE 1

The synthesis of one compound of the general formula I is carried out according to the following reaction scheme.

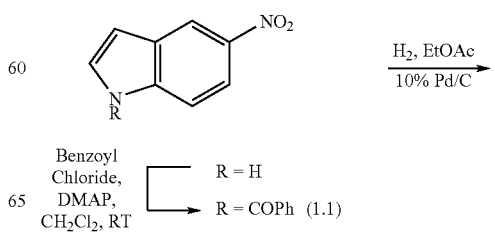

-continued

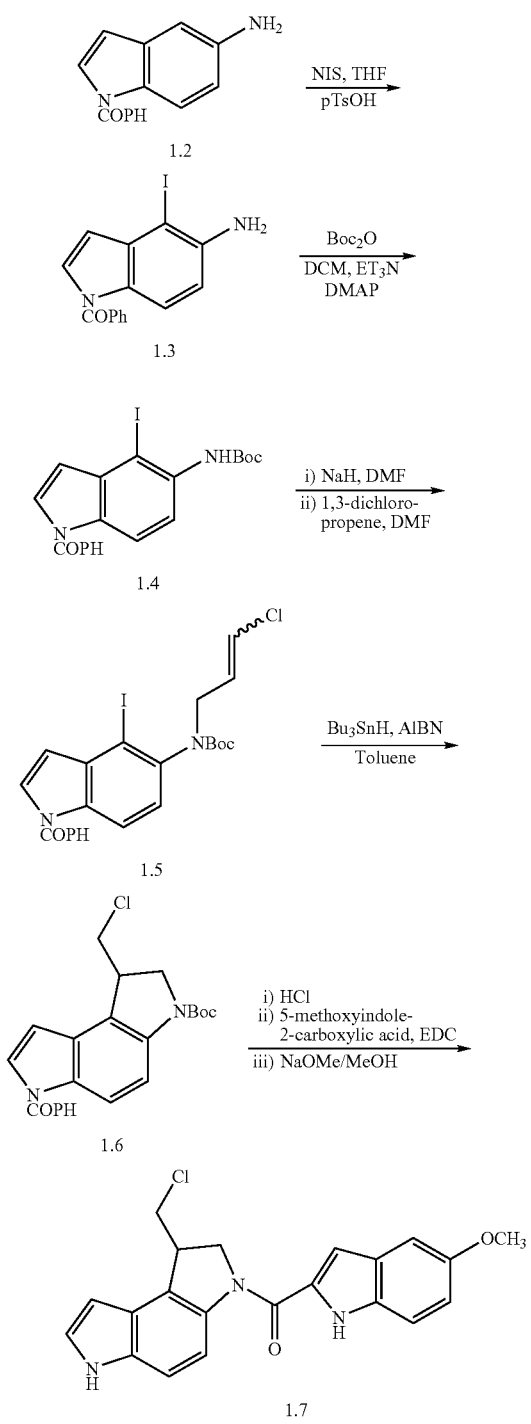

1.1 1-Benzoyl-5-nitroindole 5-nitroindole (100 mg, 0.62 mmol) in CH₂Cl₂ (1 mL) is treated with benzoyl is chloride (86 mg, 0.62 mmol, 1 equiv.) and 4-dimethylaminopyridine (74 mg, 0.62 mmol, 1 equiv.). The mixture is stirred at room temperature for 1 h, diluted with CH₂Cl₂ (10 mL), washed with HCl (1M, 2×10 mL) and water (1×10 mL), dried (MgSO₄) and concentrated. Chromatography (Silica gel, 2×15 cm, 10% ethyl acetate/hexanes) gives the product.

1.2 2-Amino-1-benzoylindole

1-Benzoyl-5-nitroindole (100 mg, 0.38 mmol) in ethyl acetate (2 mL) is treated with 10% Pd/C (10 mg) and stirred under an atmosphere of hydrogen at room temperature for 4 h. The resulting solution is filtered through celite and concentrated. Chromatography (Silica gel, 2×15 cm, 10% ethyl acetate/hexanes) gives the product.

1.3 5-Amino-1-benzoyl-4-iodoindole

5-Amino-1-benzoylindole (100 mg, 0.42 mmol) in tetrahydrofuran (THF) (1 mL) is treated with N-iodosuccinimide (103 mg, 0.46 mmol, 1.1 equiv) and 4-toluenesulfonic acid (16 mg, 0.08 mmol. 0.2 equiv.) and stirred at room temperature (RT) for 16 hours. The solution is concentrated and redissolved in ethyl acetate (10 mL). The organic layer is washed with water (1×10 is mL), 1M HCl (2×10 mL) and water (1×10 mL), dried (MgSO₄) and concentrated. Chromatography (Silica gel, 2×15 cm, 10% ethyl acetate/hexanes) gives the product.

1.4 1-Benzoyl-5-(((tert-butyloxy)carbonyl)amino-4-iodoindole

5-Amino-1-benzoyl4-iodoindole (100 mg, 0.28 mmol) is stirred in CH₂Cl₂ (2 mL) and treated with di-tert-butyl-dicarbonate (89 mg, 0.41 mmol, 1.5 equiv), triethylamine (57 μL, 0.41 mmol, 1.5 equiv) and 4-dimethylaminopyridine (4 mg, 0.028 mmol, 0.1 equiv). After 16 h at RT, the solvents are removed under reduced pressure. Chromatography (Silica gel, 2×15 cm, 10% ethyl acetate/hexanes) gives the product.

1.5 1-Benzoyl-5-[N-(3-Chloro-2-propen-1-yl)-N-((tert-butyloxy)carbonyl)]amino-4-iodoindole 1-Benzoyl-5-(tert-butyloxycarbonyl)amino-4-iodoindole (100 mg, 0.22 mmol) was stirred in DMF (1 mL) and sodium hydride (26 mg, 0.66 mmol, 60% dispersion in oil, 3 equiv.) is added. After 15 min, the suspension is treated with E/Z-1,3-dichloropropene (61 μL, 0.66 mmol, 3 equiv) and the resulting solution was stirred at RT for 16 h. The solution is concentrated and water (10 mL) is added. The aqueous solution was extracted with ethyl acetate (3×10 mL), the organic layers combined, dried and concentrated. The product was obtained after chromatography (Silica gel, 2×15 cm, 10% ethyl acetate/hexanes).

1.6 1-(Chloromethyl)-6-benzoyl-3-((tert-butyloxy)carbonyl)-1,2-dihydro-3H-pyrrolo[3,2-e]indole 1-Benzoyl-5-[N-(3-Chloro-2-propen-1-yl)-N-((tert-butyloxy)carbonyl)]amino-4-iodoindole (100 mg, 0.19 mmol), poly(methylhydrosiloxane) (200 μL), bis(tributyltin) oxide (19 μL, 0.04 mmol, 0.2 equiv) and azo isobutyronitrile (AIBN) (6 mg, 0.04 mmol, 0.2 equiv) were stirred in toluene (2 mL) at 80° C. under N₂ for 4 h. The solvent is then removed in vacuo. Chromatography (Silica gel, 2×15 cm, 10% ethyl acetate/hexanes) gives the product.

1.7 5-Methoxyindole extended agent. 1-(chloromethyl)₆-benzoyl-3-((5-methoxy-1H-indol-2-yl)carbonyl)-1,2-dihydro-3H-pyrrolo[3,2-e]indole 1-(Chloromethyl)-6-benzoyl-3-((tert-butyloxy)carbonyl)-1,2-dihydro-3H-pyrrolo[3,2-e]indole (100 mg, 0.24 mmol) is treated with a solution of hydrochloric acid in ethyl acetate (4M, 500 μL). After 30 min, the solvent is concentrated and dimethyl formamide (DMF) (1 mL) is added. The solution is treated with 1-[(3-dimethylamino)propyl]-3-ethyl carbodiimide (EDC) (140 mg, 0.73 mmol) and 5-methoxyindole-2-carboxylic acid (140 mg, 0.73 mmol). After 16 h, the solvent is removed under reduced pressure. Chromatography (Silica gel, 2×15 cm, 10% ethyl acetate/hexanes) gives the product. The 6-benzoyl protecting group may be removed by sodium methoxide in methanol, followed by removal of the solvent.

EXAMPLE 2

The following example illustrates the synthesis of a compound of the general formula 1A in which $R^1$ is $OR^8$ and $R^8$ is tBu. It is suitable for extending by a step analogous to step 1.7 above, to form a further compound of the formula IA in which $R^1$ is Ar, and optionally subsequently deprotected at the nitrogen atom of the indole ring.

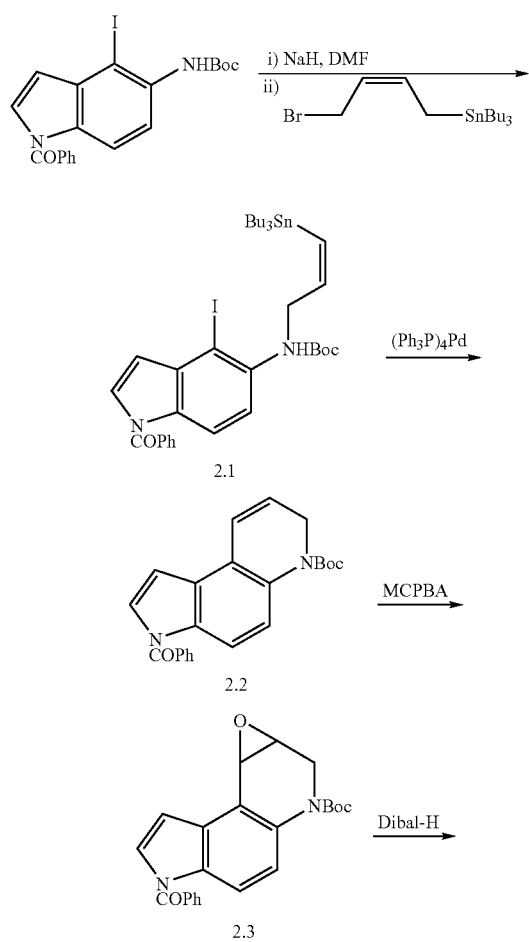

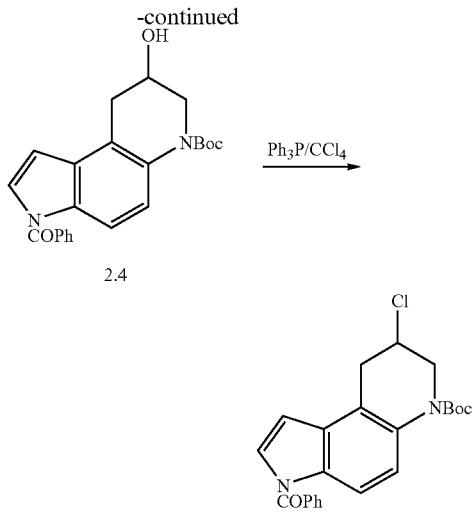

2.1 1-Benzoyl-5-[N-(3-(tributylstannyl)-2-propen-1-yl)-N-((tert-butyloxy)carbonyl)]amino-4-iodoindole 1-benzoyl-5-(tert-butyloxycarbonyl)amino-4-iodoindole (100 mg, 0.22 mmol) is stirred in DMF (1 mL) and sodium hydride (26 mg, 0.66 mmol, 60% dispersion in oil, 3 equiv.) is added. After 15 min, the suspension is treated with E/Z-1-tributylstannyl-3-bromopropene (270 mg, 0.66 mmol, 3 equiv) (Boger, D. L.; McKie, J. A.; Boyce, C. W. *Synlett* 1997, 515-516) and the resulting solution is stirred at RT for 16 h. The solution was concentrated and water (10 mL) is added. The aqueous solution is extracted with ethyl acetate (3×10 mL), the organic layers combined, dried and concentrated. The product was obtained after chromatography (Silica gel, 2 15 cm, 10% ethyl acetate/hexanes)

2.2 1,2-Dihydro-1-((tert-butyloxy)carbonyl)-5,6-(9-benzoylpyrrolo)quinoline.

1-Benzoyl-5-[N-(3-(tributylstannyl)-2-propen-1-yl)-N-((tert-butyloxy)carbonyl)]amino-4-iodoindole (100 mg, 0.12 mmol) and tetrakis(triphenylphosphine)palladium(0) (32 mg, 0.2 equiv) are stirred in toluene (2 mL) at 50° C. under $N_2$ for 2 h. The solvent is then removed in vacuo. Chromatography (Silica gel, 2×15 cm, 10% ethyl acetate/hexanes) gives the product.

2.3 3,4-Epoxy-1-((tert-butyloxy)carbonyl)-1,2,3,4-tetrahydro-5,6-(9-benzoylpyrrolo)quinoline.

1,2-dihydro-1-((tert-butyloxy)carbonyl)-5,6-(9-benzoylpyrrolo)quinoline. (100 mg, 0.27 mmol) and 3-chloroperoxy benzoic acid (68 mg, 0.40 mmol, 1.5 equiv) were stirred in $CH_2Cl_2$ (2 mL) at −78° C. to −30° C. under $N_2$ for 2 h. The solvent is then removed in vacuo. Chromatography (Silica gel, 2×15 cm, 10% ethyl acetate/hexanes) gives the product.

2.4 4-Hydroxy-1-((tert-butyloxy)carbonyl)-1,2,3,4-tetrahydro-5,6-(9-benzoyl)pyrroloquinoline.

3,4-epoxy-1-((tert-butyloxy)carbonyl)-1,2,3,4-tetrahydro-5,6-(9-benzoylpyrrolo)quinoline (100 mg, 0.26 mmol)

was treated with disobutyl aluminium hydride (Dibal-H) (55 mg, 0.39 mmol, 1.5 equiv) in THF (2 mL), at −78° C. to −30° C. under N₂. After 1 h, the reaction is quenched by the addition of water (2 mL) and the resulting solution is extracted with ethyl acetate (3×10 mL), the organic layers combined, dried and concentrated. The solvent is removed in vacuo. Chromatography (Silica gel, 2×15 cm, 10% ethyl acetate/hexanes) gives the product.

2.5 4-Chloro-1-((tert-butyloxy)carbonyl)-1,2,3,4-tetrahydro-5,6-(9-benzoyl)pyrroloquinoline 4-hydroxy-1-((tert-butyloxy)carbonyl)-1,2,3,4-tetrahydro-5,6-(9-benzoyl)pyrroloquinoline (100 mg, 0.26 mmol) in CH₂Cl₂ (2 mL) is treated with a prepared solution of PPh₃ (137 mg, 0.52 mmol, 2 equiv) and CCl₄ (200 mL) in CH₂Cl₂ (2 mL) at RT. After 4 h, the solvent is removed in vacuo. Chromatography (Silica gel, 2×15 cm, 10% ethyl acetate/hexanes) gives the product.

EXAMPLE 3

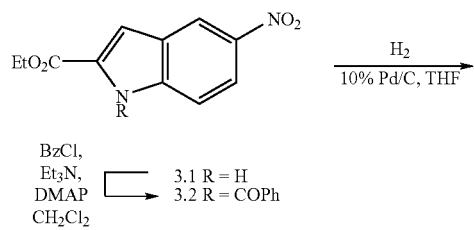

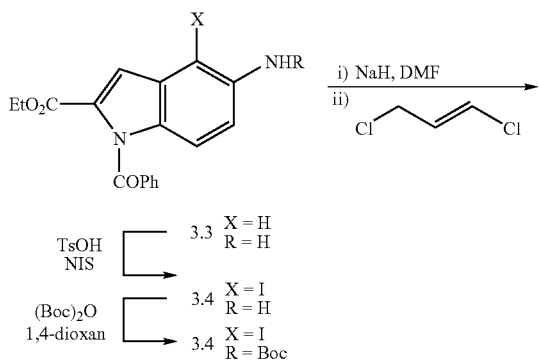

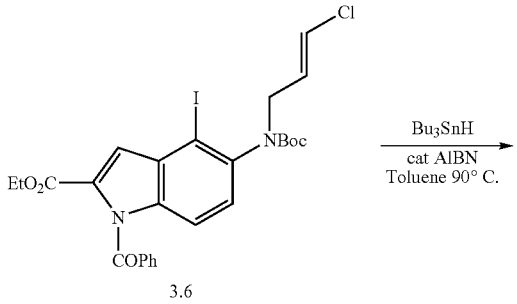

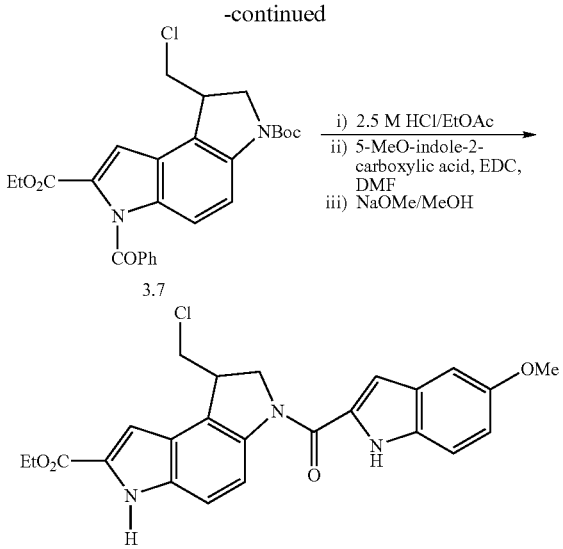

3.1 Ethyl 1-benzoyl-5-nitroindole-2-carboxylate (3.2)

Ethyl 5-nitroindole-2-carboxylate (3.1) (1.5 g, 6.41 mmol) in CH₂Cl₂ (30 ml) was treated with benzoyl chloride (1.19 ml, 10.26 mmol), Et₃N (891 μl, 6.41 mmol) and DMAP (783 mg, 6.41 mmol). The mixture was stirred for 16 h. 10% NaHCO₃ (10 ml) and CH₂Cl₂ (10 ml) were added and the organic layer was separated. The aqueous layer was extracted with CH₂Cl₂ (3×5 mL). The combined organic layers were washed with H₂O (10 ml), 5% HCl (10 ml) and H₂O (10 ml). The solution was dried (MgSO₄) and concentrated. The 10 residue was crystalised from EtOAc/Hex 1:9 to afford 1.85 g (87%) of 3.2 as a yellow powder: ¹H NMR (250 MHz, CDCl₃) δ ppm 8.66 (d, 1H), 8.25 (d, 1H), 7.80 (d,1H), 7.6-7.72 (m, 3H), 7.48 (m, 3H), 4.00 (q, 2H), 1.10 (t, 3H). FABMS (NBA/NaI) m/z 339 (M+H⁺ expected 339)

3.2 Ethyl 5-amino-1-benzoylindole-2-carboxylate (3.3).

A solution of 3.2 (1.86 g, 5.5 mmol) and 10% Pd/C (440 mg) in dry THF (30 ml) was stirred under H₂ for 16 hrs. The resulting mixture was filtered through celite which was washed with EtOAc (40 ml) and the filtrate was concentrated. The residue was purified by chromatography (SiO₂, 0 to 40% EtOAc in hexanes) to afford 3.3 (1.63 g, 96%) as a bright yellow oil. ¹H NMR (250 MHz, CDCl₃) δ ppm 7.40-7.72 (m, 6H), 7.18 (s, 1H), 6.92 (d, 1H), 6.82 (dd, 1H), 3.92 (q, 2H), 3.68 (br s, 2H), 1.06 (t, 3H); FABMS: (NBA/NaI) m/z 308 (M+H⁺ expected 308).

3.3 Ethyl 5-amino-1-benzoyl-4-iodoindole-2-carboxylate (3.4)

5-amino-1-benzoylindole (1.63 g, 5.29 mmol) in THF (75 mL) was treated with N-iodosuccinimide (1.89 g, 8.46 mmol) and 4-toluenesulfonic acid (364 mg, 2.12 mmol) and stirred at RT for 16 hours. The solution was concentrated and redissolved in ethyl acetate (100 mL). The organic layer was washed with water (1×100 mL), 1 M HCl (2×100 mL) and water (1×100 mL), dried (MgSO$_4$) and concentrated. Chromatography (SiO$_2$, 10% ethyl acetate/hexanes) gave the product (1.17 g, 51%) as a bright yellow solid. $^1$H NMR (250 MHz, CDCl$_3$) δ ppm 7.30-7.70 (m, 6H), 7.30 (s, 1 H), 6.80 (d, 1 H), 4.05 (s, 2 H), 3.85 (q, 2 H), 1.0 (t, 3H) FABMS (NBA/NaI) m/z 434 (M+H$^+$ expected 434),457 (M+Na$^+$ expected 457).

3.4 Ethyl 1-benzoyl-5-(N-(tert-butyloxycarbonyl)-4-iodoindole-2-carboxylate (3.5)

A mixture of 3.4 (1.17 g, 2.70 mmol), (Boc)$_2$O (9.40 g, 43 mmol) and Et$_3$N (375 μL, 2.70 mmol) in dioxan (100 mL) was heated to 100° C. under N$_2$ for 48 h. Upon completion, the solution was cooled, concentrated and purified by flash chromatography (SiO$_2$, 0-20% EtOAc in hexane) to afford 3.5 (1.3 g, 90%) as a yellow oil. FABMS (NBA.NaI) 535 (M+H$^+$ expected 535).

3.5 Ethyl 1-benzoyl-5-[N-(3-chloro-2-propen-1-yl)-N-((tert-butyloxy)carbonyl)]amino-4-iodoindole (3.6)

1-benzoyl-5-(tert-butyloxycarbonyl)amino-4-iodoindole (100 mg, 0.22 mmol) was stirred in DMF (1 mL) and sodium hydride (26 mg, 0.66 mmol, 60% dispersion in oil, 3 equiv.) was added. After 15 min, the suspension was treated with E/Z-1,3-dichloropropene (61 μL, 0.66 mmol, 3 equiv) and the resulting solution was stirred at RT for 16 h. The solution was concentrated and water (10 mL) was added. The aqueous solution was extracted with ethyl acetate (3'10 mL), the organic layers combined, dried and concentrated. The (3.6) product was obtained after chromatography (SiO$_2$, 10% ethyl acetate/hexanes) as a yellow oil (125 mg, 94%). FABMS (NBA/NaI) m/z 609 (M+H$^+$ expected 609).

3.6 Ethyl 6-benzoyl-1-(chloromethyl)-3-((tert-butyloxy)carbonyl)-1,2-dihydro-3H-pyrrolo[3,2-e]indole-7-carboxylate (3.7)

Compound 3.6 (100 mg, 0.19 mmol), and AIBN (6 mg, 0.04 mmol, 0.2 equiv) were stirred in toluene (2 mL) at 80° C. under N$_2$. Bu$_3$SnH (51 μL, 0.19 mmol) was added in 4 portions over 1 h. The solvent was then removed in vacuo. Chromatography (SiO$_2$ 10% ethyl acetate/hexanes) gave the product (3.9) (72 mg, 78%) as an oil. FABMS (NaI/NBA) m/z 483 (M+H+expected 483).

3.7 Ethyl 1-(chloromethyl)-3-((5-methoxy-1H-indol-2-yl)carbonyl)-1,2-dihydro-3H-pyrrolo[3,2-e]indole-7-carboxylate (3.8)

Compound 3.7(100 mg, 0.21 mmol) was treated with a solution of hydrochloric acid in ethyl acetate (4M, 500 μL). After 30 min, the solvent was concentrated and DMF (1 mL) was added. The solution was treated with EDC (120 mg, 0.63 mmol) and 5-methoxyindole-2-carboxylic acid (120 mg, 0.63 mmol). After 16 h, the solvent was removed under reduced pressure and the residue (the 6N-benzoyl protected precursor of compound 3.8) was dissolved in CH$_3$OH (1 mL). A solution of NaOCH$_3$ in CH$_3$OH (2M, 100 μL) was then added and the solution stirred for 10 minutes. The solvent was removed and chromatography (SiO$_2$, 10% ethyl acetate/hexanes) gave the product (3.8) (100 mg, 86%). FABMS (NBA/NaI) m/z 557 (M+H$^+$ expected 557).

EXAMPLE 4

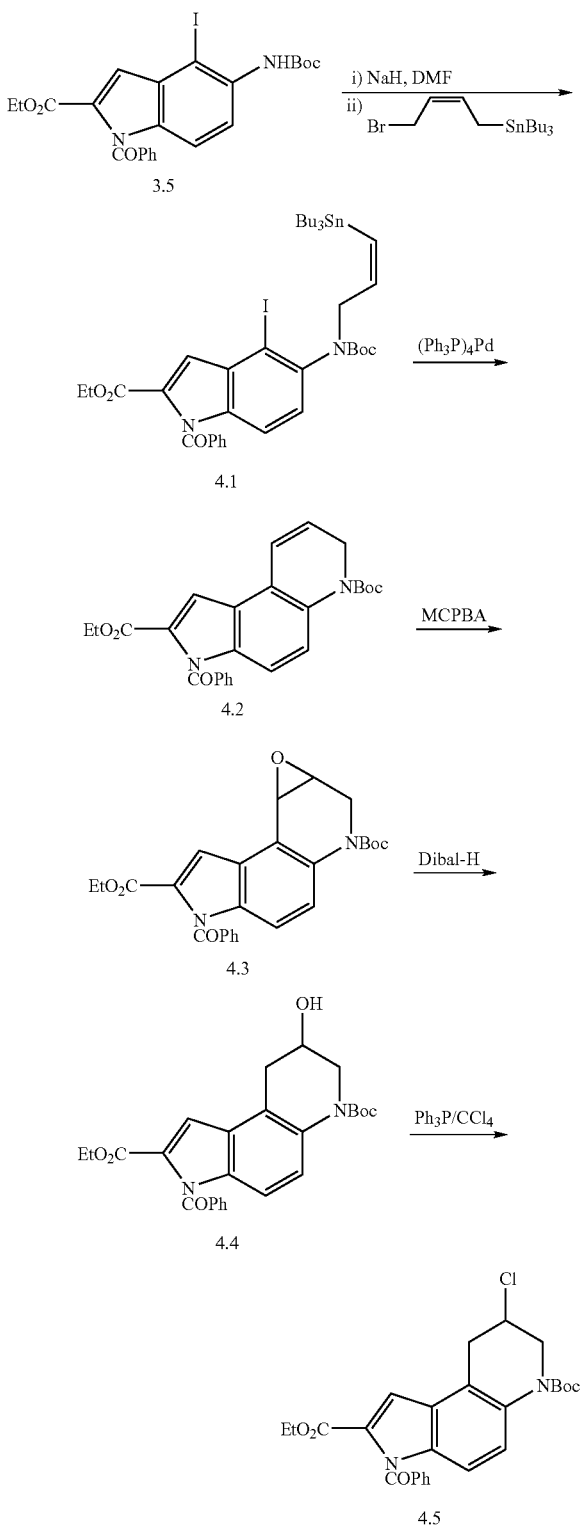

4.1 Ethyl 1-Benzoyl-5-[N-(3-(tributylstannyl)-2-propen-1-yl)-N-(((tert-butyloxy)carbonyl)]amino-4-iodoindole-7-carboxylate (4.1)

Ethyl 1-benzoyl-5-(tert-butyloxycarbonyl)amino-4-iodoindole (3.5, synthesised as described in Example 3.1-3.4) (100 mg, 0.18 mmol) was stirred in DMF (1 mL) and sodium hydride (21 mg, 0.54 mmol, 60% dispersion in oil, 3 equiv.) was added. After 15 min, the suspension was treated with E/Z-1-tributylstannyl-3-bromopropene (221 mg, 0.54 mmol, 3 equiv) and the resulting solution was stirred at RT for 16 h. The solution was concentrated and water (10 mL) was added. The aqueous solution was extracted with ethyl acetate (3×10 mL), the organic layers combined, dried and concentrated. The product was obtained after chromatography ($SiO_2$, 10% ethyl acetate/hexanes) as a colourless solid (132 mg, 92%). FABMS (NBA/NaI) m/z 792 ($M+H^+$ expected 792).

4.2 5,6-(9-Benzoyl-8-(ethyloxy)carbonylpyrrolo)-1-((tert-butyloxy)carbonyl)-2,4-dihydroquinoline (4.2)

Compound 4.1 (100 mg, 0.12 mmol) and tetrakis(triphenylphosphine)palladium(0) (32 mg, 0.2 equiv) were stirred in toluene (2 mL) at 50° C. under $N_2$ for 2 h. The solvent was then removed in vacuo. Chromatography ($SiO_2$, 10% ethyl acetate/hexanes) gave the product (50 mg, 94%) as a yellow oil. FABMS (NBA/NaI) m/z 447 ($M+H^+$ expected 447).

4.3 5,6-(9-benzoyl-8-(ethyloxy)carbonylpyrrolo)-1-((tert-butyloxy)carbonyl)-3,4-epoxy-1,2,3,4-tetrahydroquinoline (4.3)

Compound 4.2 (100 mg, 0.22 mmol) and MCPBA (57 mg, 0.33 mmol, 1.5 equiv) were stirred in $CH_2Cl_2$ (2 mL) at −30° C. under $N_2$ for 2 h. The solvent was then removed in vacuo. Chromatography ($SiO_2$, 10% ethyl acetate/hexanes) gave the product (70 mg, 69%) as an oil. FABMS (NBA/NaI) m/z 463 ($M+H^+$ expected 463).

4.4 5,6-(9-benzoyl-8-(ethyloxy)carbonylpyrrolo)-1-((tert-butyloxy)carbonyl)-4-hydroxy-1,2,3,4-tetrahydroquinoline (4.4)

Compound 4.3 (100 mg, 0.22 mmol) was treated with Dibal-H (46 mg, 0.33 mmol, 1.5 equiv) in THF (2 mL), at −30° C. under $N_2$. After 1 h, the reaction was quenched by the addition of water (2 mL) and the resulting solution was extracted with ethyl acetate (3×10 mL), the organic layers combined, dried and concentrated. The solvent was removed in vacuo. Chromatography ($SiO_2$, 10% ethyl acetate/hexanes) gave the alcohol (85 mg, 83%). FABMS (NBA/NaI) m/z 465 ($M+H^+$ expected 465).

4.5 5,6-(9-benzoyl-8-(ethyloxy)carbonylpyrrolo)-1-((tert-butyloxy)carbonyl)-4-chloro-1,2,3,4-tetrahydroquinoline (4.5)

Compound 4.4 (100 mg, 0.22 mmol) in $CH_2Cl_2$ (2 mL) was treated with a prepared solution of $PPh_3$ (116 mg, 0.44 mmol, 2 equiv) and $CCl_4$ (200 μL) in $CH_2Cl_2$ (2 mL) at RT. After 24 h, the solvent was removed in vacuo. Chromatography ($SiO_2$, 10% ethyl acetate/hexanes) gave the target compound as an oil (95 mg, 90%). FABMS (NBA/NaI) m/z 484 ($M+H^+$ expected 484). The compound may be deprotected by removal of the tBOC group, a DNA-binding sub-unit conjugated to the nitrogen atom of the tCtra hydroquinoline ring and the indole nitrogen subsequently deprotected by steps analogous to those of Example 3.7.

EXAMPLE 5

Biological Testing of Ethyl 1-(chloromethyl)-3-((5-methoxy-1H-indol-2-yl)carbonyl)-1,2-dihydro-3H-pyrrolo[3,2-e]indole-7-carboxylate (3.8)

Materials and Methods

5.1 Incubation Mixtures of Compound and Microsomes

Test compound (synthesised in example 3) activation by CYP enzymes was carried out using NADPH supplemented rat liver microsomes; Incubation mixtures comprised microsomal protein (1 mg/ml), reduced-nicotinamide adenine dinucleotide phosphate (NADPH, 10 mM) and phosphate buffer (pH7.4, 100 mM). Test compound (0.01-100 μM final concentration) in DMSO (20 μl) was added to the microsomal incubation mixtures (0.5 ml) and incubated for 60 min at 37C. Control incubates contained test compound and microsomal incubation mixture terminated at 0 time. All incubations were terminated by addition of an equal volume of ice-cold acetonitrile and microfuged for 3 min. Aliquots of the supernatant were added to cells in culture.

5.2 Cell Culture Based Cytotoxicity Measurement

Chinese Hamster Ovary (CHO) cell were grown in MEM supplemented with. 10% dialysed FBS and G418 (400 μg/ml). All cells were seeded at an initial density of 1000 cells/well in 96-well-plates, incubation at 37° C. for 24 hours. Aliquots (0.1 ml) of the test compound/microsomal/acetonitrile supernatnant was then added to the CHO cells. Cells were then incubated for 24 hours at 37° C., 5% $CO_2$. After this time period MTT (50 μl; 2 mg/ml stock solution) was added to each well and cells were incubated for a further 4 hours. During this time period MTT, a hydrogen acceptor tetrazolium salt, is reduced to formazan dye by mitochondrial dehydrogenase of viable cells. The media was aspirated from cells and DMSO (100 μl/well) added to solubilise the coloured formazan dye. Absorbance of the formazan dye in the 96-well-plates was then determined at 550 nm. The effect of microsomal activation by the test compound on the arrest of CHO cell growth could be determined by comparing the $IC_{50}$ (concentration that inhibited cell growth by 50%) with and without microsomal incubation.

| | Results | | |
|---|---|---|---|
| | CHO IC50 (μM) | | |
| compound | +activation | −activation | AF |
| 3.8 | 0.06 ± 0.02 | 4.3 ± 0.41 | 71.7* |

Effect of compound 3.8 and its metabolism (activation) product on the survival of Chinese hamster ovary cells in culture. Cells were incubated for 24 hours with supernatants from reaction mixtures of compound 3.8 with NADPH fortified rat liver microsomes. $IC_{50}$ represents the concentration of drug required to inhibit cell growth by 50%. Values are expressed as the mean±sd for three experiments. See methods

The invention claimed is:

1. A pharmaceutical composition comprising a compound of the general formula I and a pharmaceutically acceptable excipient in which B is CH;

Z is NH;

the or each $R^{11}$ is selected from the group consisting of —OH, $C_{1-4}$ alkoxy, $C_{1-4}$ alkyl, —$NO_2$, —CN, Cl, Br, I, —$NHCOR^{15}$, and $COOR^{16}$;

n is an integer in the range 0 to 4;

$R^{12}$ is selected from the group consisting of H, —$CONH_2$, and —$COR^{16}$;

the or each $R^{13}$ is selected from the group consisting of OH and $C_{1-4}$ alkoxy;

m is 0, 1 or 2;

$R^{15}$ is $C_{1-4}$ alkyl; and $R^{16}$ is $C_{1-4}$ alkyl.

2. A compound of the general formula II or a salt thereof

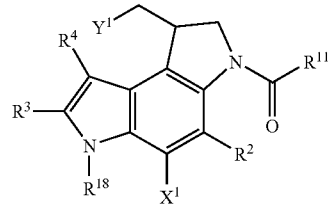

II in which
$R^2$ is H;
$R^4$ is selected from the group consisting of H, $C_{1-4}$ alkyl, and —$COOR^9$;
$R^3$ is selected from the group consisting of H, $C_{1-4}$ alkyl, and —$COOR^9$;
$R^9$ is $C_{1-4}$ alkyl;
$X^1$ is H;

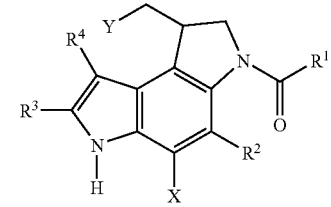

I in which X is H;
Y is Cl, Br, or I;
$R^1$ is —Ar;
$R^2$ is H;
$R^4$ is selected from the group consisting of H, $C_{1-4}$ alkyl, Cl, Br, I, and —$COOR^9$;
$R^3$ is selected from the group consisting of H, $C_{1-4}$ alkyl, and —$COOR^9$;
$R^9$ is $C_{1-4}$ alkyl;

Ar is selected from the group consisting of

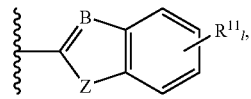

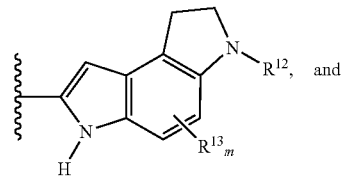

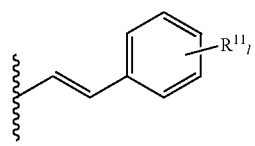

$Y^1$ is Cl, Br, or I;

$R^{18}$ is H or an amine protecting group selected from the group consisting of benzyl, benzoyl, benzyloxycarbonyl, t-butyloxycarbonyl, fluorenyl-N-methoxycarbonyl and 2-[biphenylyl-(4)]-propyl-2-oxycarbonyl;

$R^{17}$ is $Ar^2$;

$Ar^2$ is selected from the group consisting of:

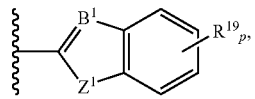

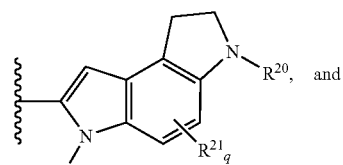

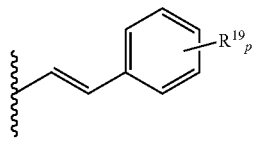

in which $B^1$ is CH;

$Z^1$ is $NR^{18}$;

the or each $R^{19}$ is selected from the group consisting of OH, $C_{1-4}$ alkoxy $C_{1-4}$ alkyl, $NO_2$, —CN, Cl, Br, I, —$NHCOR^{22}$, and —$COOR^{23}$;

p is an integer in the range 0 to 4;

$R^{20}$ is selected from the group consisting of H, —$CONH_2$, and —$COR^{23}$;

the or each $R^{21}$ is selected from OH and $C_{1-4}$ alkoxy;

q is 0, 1 or 2;

$R^{22}$ is $C_{1-4}$ alkyl; and $R^{23}$ is $C_{1-4}$ alkyl.

3. A compound according to claim 2 in which the or each $R^{18}$ is H.

4. A compound according to claim 2 in which $Y^1$ is Cl.

5. A compound according to claim 2 in which $R^3$ is H or COOMe.

6. A compound according to claim 2 in which $R^4$ is H.

7. A compound selected from the group consisting of:

1-(chloromethyl)-6-benzoyl-3-((tert-butyloxy)carbonyl)-1,2-dihydro-3H-pyrrolo [3,2-e]indole;

1-(chloromethyl)-6-benzoyl-3-((5-methoxy-1H-indol-2-yl)carbonyl)-1,2-dihydro-3H-pyrrolo[3,2-e]indole;

1-(chloromethyl)-3-((5-methoxy-1H-indol-2-yl)carbonyl)-1,2-dihydro-3H-pyrrolo[3,2-e]indole;

ethyl 6-benzoyl-1-(chloromethyl)-3-((tert-butyloxy)carbonyl)-1,2-dihydro-3H-pyrrolo[3,2-e]indole-7-carboxylate;

ethyl 6-benzoyl-1-(chloromethyl)-3-((5-methoxy-1H-indol-2-yl)carbonyl)-1,2-dihydro-3H -pyrrolo[3,2-e]indole-7-carboxylate; and ethyl 1-(chloromethyl)-3-((5-methoxy-1H-indol-2-yl)carbonyl)-1,2-dihydro-3H-pyrrolo[3,2-e]indole-7-carboxylate.

8. A pharmaceutical composition comprising a compound according to claim 2 and a pharmaceutically acceptable excipient.

9. A compound of the general formula III

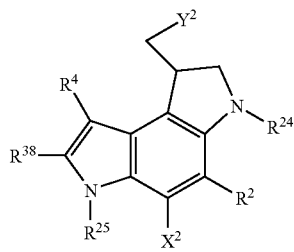

in which $R^2$ is H;

$R^4$ is selected from the group consisting of H, $C_{1-4}$ alkyl, and —COOR$^9$;

$R^9$ is $C_{1-4}$ alkyl;

$R^{38}$ is selected from the group consisting of H, $C_{1-4}$ alkyl, and —COOR$^9$;

$X^2$ is H;

$Y^2$ is Cl, Br, or I; and $R^{24}$ and $R^{25}$ are each H or an amine protecting group selected from the group consisting of benzyl, benzoyl, benzyloxycoarbonyl, t-butyloxycarbonyl, fluorenyl-N-methoxycarbonyl and 2-[biphenylyl-(4)]-propyl-2-oxy-carbonyl.

10. A compound according to claim 9 in which $R^{24}$ and $R^{25}$ are different from one another.

11. A compound according to claim 10 in which $R^{24}$ is butyloxycarbonyl and $R^{25}$ is —COPh.

12. A compound according to claim 9 in which $Y^2$ is Cl.

\* \* \* \* \*